US012681195B2

(12) United States Patent
Cortina Gil et al.

(10) Patent No.: US 12,681,195 B2
(45) Date of Patent: Jul. 14, 2026

(54) RADIOGRAPHIC IMAGING BASED ON DETECTION OF IONIZING PARTICLES

(71) Applicant: UNIVERSITE CATHOLIQUE DE LOUVAIN, Louvain-la-Neuve (BE)

(72) Inventors: Eduardo Cortina Gil, Louvain-la-Neuve (BE); Andrea Giammanco, Louvain-la-Neuve (BE); Samip Basnet, Louvain-la-Neuve (BE); Sophie Wuyckens, Louvain-la-Neuve (BE)

(73) Assignee: UNIVERSITE CATHOLIQUE DE LOUVAIN, Louvain-la-Neuve (BE)

( * ) Notice: Subject to any disclaimer, the term of this patent is extended or adjusted under 35 U.S.C. 154(b) by 163 days.

(21) Appl. No.: 18/699,082

(22) PCT Filed: Oct. 11, 2022

(86) PCT No.: PCT/EP2022/078291
§ 371 (c)(1),
(2) Date: Apr. 5, 2024

(87) PCT Pub. No.: WO2023/062027
PCT Pub. Date: Apr. 20, 2023

(65) Prior Publication Data
US 2024/0402364 A1 Dec. 5, 2024

(30) Foreign Application Priority Data
Oct. 11, 2021 (EP) .................................... 21208157

(51) Int. Cl.
*G01T 1/185* (2006.01)
*A61B 6/42* (2024.01)
(52) U.S. Cl.
CPC ............ *G01T 1/185* (2013.01); *A61B 6/4233* (2013.01); *A61B 6/4266* (2013.01)

(58) Field of Classification Search
CPC ...... G01T 1/185; A61B 6/4233; A61B 6/4266
See application file for complete search history.

(56) References Cited

U.S. PATENT DOCUMENTS 7,858,949 B2 * 12/2010 Bolotnikov ............. H01J 47/02
250/385.1
10,451,745 B1 10/2019 Bonal et al.
(Continued)

FOREIGN PATENT DOCUMENTS

EP 2749903 A1 * 7/2014 ............... G01T 1/17

OTHER PUBLICATIONS

A portable, gas-tight, and compact glass-RPC telescope for muon imaging (Year: 2020).*
(Continued)

*Primary Examiner* — Uzma Alam
*Assistant Examiner* — Fani Polyzos Boosalis
(74) *Attorney, Agent, or Firm* — KARCESKI IP LAW, PLLC

(57) ABSTRACT

In an ionizing particle detection module, an ionizing particle traversing an ionization chamber produces a local ionization in an ionizable medium within the ionization chamber. A matrix of detection pads face the ionization chamber so that respective detection pads cover respective zones in the ionization chamber. Respective detection channels comprise respective mutually exclusive groups of detection pads. A detection channel provides an indication of a local ionization occurring somewhere within the respective zones in the ionization chamber covered by the respective detection pads of the detection channel. A cluster of detection pads is identified among the detection pads belonging to detection channels simultaneously providing indications of local ionization. A traversing point indication is provided on the basis of the cluster that has been identified if the cluster comprises
(Continued)

101

103 a predefined minimum number of detection pads. The traversing point indication indicating where the ionizing particle has traversed the ionization chamber.

15 Claims, 3 Drawing Sheets

(56) References Cited

U.S. PATENT DOCUMENTS

| | | | |
|---|---|---|---|
| 10,617,889 B1 * | 4/2020 | Galyaev | ............... A61N 5/1077 |
| 2004/0000630 A1 * | 1/2004 | Spartiotis | ............. G01T 1/2964 |
| | | | 250/208.1 |

OTHER PUBLICATIONS

Giammanco Andrea et al: "A portable, gas-tight, and compact glass-RPC telescope for muon immaging," XV Workshop on Resistive Plate Chambers and Related Detectors, Feb. 14, 2020.

International Search Report and Written Opinion dated Jan. 3, 2023, for International Patent Application No. PCT/EP2022/078291.

Kunihiro Morishima et al: "Discovery of a big void in Khufu's Pyramid by observation of cosmic-ray muons," arxiv.org, Cornell University Library, 201 Olin Library Cornell University, Ithaca, NY 14853, Nov. 5, 2017.

Procureur S et al: "Genetic multiplexing and first results with a 50x50cm2Micromegas," Nuclear Instruments & Methods in Physics Research, Section A, vol. 729, Aug. 31, 2013, pp. 888-894.

Sophie Wuyckens et al: "A portable muon telescope based on small and gas-tight Resistive Plate Chamgers," arxiv.org, Cornell University Library, 201 Olin Library, Cornell University, Ithaca, NY 14853, Jun. 18, 2018.

* cited by examiner

100

101

104

301          302

303          304

500

600

RADIOGRAPHIC IMAGING BASED ON DETECTION OF IONIZING PARTICLES

CROSS-REFERENCE TO RELATED APPLICATION(S)

This is a National Stage Entry into the United States Patent and Trademark Office from International Patent Application No. PCT/EP2022/078291, filed on Oct. 11, 2022, which relies on and claims priority to European Patent Application No. 21208157.6, filed on Oct. 11, 2021; the entire contents of both of which are incorporated herein by reference.

FIELD OF THE INVENTION

An aspect of the invention relates to an ionizing particle detection module for detection of ionizing particles that have traversed an object to be imaged. The ionizing particles may be, for example, muons. The ionizing particle detection module may form part of a radiographic imaging system, such as, for example, one that is referred to as muon telescope, muograph, or muoscope. Other aspects of the invention relate to a radiographic imaging system and the use thereof, as well as a method of radiographic imaging based on detection of ionizing particles that have traversed an object to be imaged.

BACKGROUND OF THE INVENTION

An object may be imaged by detecting ionizing particles that have traversed the object. The ionizing particles may be muons. Muons are produced in an upper part of the atmosphere by cosmic rays. Muons have a relatively large penetrating power. As a result, muons may traverse relatively large objects, such as, for example, cargos, buildings, and even mountains. At sea level, muons arrive at a rate of about 100 Hz/m2. Imaging based on muons is generally referred to by the neologism "muography". Other terms are also used, such as, for example, "muon radiography", "muon tomography", and "cosmic ray radiography".

There are two basic muography techniques: absorption-based muography and scattering-based muography. In absorption-based muography, muons are detected on one side with respect to an object to be imaged. Imaging is based on a probability for a muon to pass through the object. In scattering-based muography, muons are detected on two opposite sides of an object to be imaged. A trajectory of a muon is detected before and after passing the object. Imaging is based on scattering of muons that have traversed the object.

Muography, whether it is absorption-based or scattering-based, may take a relatively long time. It may take several hours to image a relatively small object. It may take several weeks to image a relatively large object. This is because of the relatively low rate at which muons arrive. An orientation of the object also plays a role because most muons arrive preferentially from angles close to zenith.

Muography generally involves a detection module that detects an incident muon and that indicates where the incident muon has traversed the detection module. The detection module may comprise a so-called glass resistive plate chamber. Basically, a glass resistive plate chamber is a chamber comprised between a pair of parallel glass plates that are provided with resistive outer layers. The chamber contains an ionizable gas. A relatively high voltage is applied between the resistive outer layers of the parallel glass plates. This creates a relatively strong electrical field in the chamber filled with the ionizable gas. A muon traversing the chamber leaves a trail of ionized gas in its wake. This trail of ionized gas may be detected by means of conductive strips facing one of the parallel glass plates.

A detection module typically comprises two glass resistive plate chambers. One of the two glass resistive plate chambers comprises an array of conductive strips in an X direction. The other glass resistive plate chamber comprises an array of conductive strips in an Y direction, that is, orthogonal to the X direction. A muon traversing the two glass resistive plate chambers will cause a local ionization in each of these chambers. In the one chamber, this will induce a signal in one of the conductive strips in the X direction. In the other chamber, this will induce a signal in one of the conductive strips in the Y direction. The conductive strip in the X direction and the conductive strip in the Y direction in which these respective signals are induced indicate where the muon has traversed the detection module.

In order to detect a trajectory of a muon, two detection modules as described hereinbefore are required. Each detection module indicates where the muon has traversed the detection module concerned. An angle of incidence in azimuth direction and an angle of incidence in elevation direction can be determined on the basis of these indications. These angles indicate the trajectory of the muon traversing the two detection modules. Thus, detection of a muon trajectory involves four glass resistive plate chambers.

Patent publication U.S. Ser. No. 10/451,745B1 is an example of the state-of-the-art. This publication describes a muon detector system capable of determining muon direction and flight trajectory or path. The muon detector system includes scintillators for determining muon direction, and an array of muon detectors arranged in orthogonal layers for determining flight trajectory. The system can be used for tomographic and telescopic mode imaging, and may be used for imaging concealed and/or subterranean objects.

The article by Procureur S. et al. entitled "Genetic multiplexing and first results with a 50×50 cm$^2$ Micromegas" published in Nuclear Instruments & Methods in Physics Research, Section A, Vol. 729, at pages 888-894, is another example of the state-of-the-art. The article states that it turns out that in Micromegas detectors, and more generally in any Micro-Pattern Gaseous Detectors (MGDP), a particle usually leaves a signal on several neighboring strips. This feature clearly carries a redundancy, and can be utilized to localize the particles with an appropriate grouping pattern. Suppose indeed that two neighboring strips i and i+1 are connected to two given channels a and b, and each of these channels is in turn connected to several other strips. The connection is made in such a way that there is only one set of two consecutive strips for a given set of two channels. Therefore if a signal is recorded only on channels a and b, it is almost certain that it results from the passage of a particle close to strips i and i+1. This so-called genetic multiplexing is also described in patent publication EP2749903A1.

SUMMARY OF THE INVENTION

There is a need for an ionizing particle detection module that allows improvement in at least one of the following aspects: compactness, lightweight, ease of use, spatial resolution, low cost, and low power consumption.

An aspect of the invention provides for an ionizing particle detection module comprising:

an ionizing particle detector comprising:

an ionization chamber adapted to produce a local ionization in an ionizable medium within the ionization chamber in response to an ionizing particle traversing the ionization chamber;

a matrix of detection pads facing the ionization chamber so that respective detection pads cover respective zones in the ionization chamber;

a plurality of detection channels wherein respective detection channels comprise respective mutually exclusive groups of detection pads according to the following rules:

the detection pads of a detection channel are nonadjacent and dispersed throughout the matrix;

two detection channels have a maximum of two detection pads next to each other in the matrix, one of the two detection pads belonging to one of the two detection channels, the other of the two detection pads belonging to the other of the two detection channels, a detection channel being adapted to provide an indication of a local ionization occurring somewhere within the respective zones in the ionization chamber covered by the respective detection pads of the detection channel;

a traversing point locator adapted to identify a cluster among the detection pads belonging to detection channels simultaneously providing indications of local ionization, and adapted to provide a traversing point indication on the basis of the cluster that has been identified if the cluster comprises a predefined minimum number of detection pads, the traversing point indication indicating where the ionizing particle has traversed the ionization chamber.

A further aspect of the invention provides for a radiographic imaging system adapted to image an object based on detection of ionizing particles that have traversed the object, the radiographic imaging system comprising at least one ionizing particle detection module as defined hereinbefore.

Yet a further aspect of the invention provides for the use of such a radiographic imaging system for imaging an object, whereby muons constitute the ionizing particles that traverse the object and that are detected.

Yet a further aspect of the invention provides for a method of radiographic imaging based on detection of ionizing particles that have traversed an object to be imaged, wherein use is made of:

an ionizing particle detector comprising:

an ionization chamber adapted to produce a local ionization in an ionizable medium within the ionization chamber in response to an ionizing particle traversing the ionization chamber;

a matrix of detection pads facing the ionization chamber so that respective detection pads cover respective zones in the ionization chamber;

a plurality of detection channels wherein respective detection channels comprise respective mutually exclusive groups of detection pads that are electrically interconnected with each other according to the following rules:

the detection pads of a detection channel are nonadjacent and dispersed throughout the matrix;

two detection channels have a maximum of two detection pads next to each other, one of the two detection pads belonging to one of the two detection channels, the other of the two detection pads belonging to the other of the two detection channels, a detection channel being adapted to provide an indication of a local ionization occurring somewhere within the respective zones in the ionization chamber covered by the respective detection pads of the detection channel, the method comprising:

identifying a cluster of detection pads among the detection pads belonging to detection channels simultaneously providing indications of local ionization; and providing a traversing point indication on the basis of the cluster that has been identified if the cluster comprises a predefined minimum number of detection pads, the traversing point indication indicating where the ionizing particle has traversed the ionization chamber.

In each of these aspects, a single ionizing particle detection module comprising a single ionization chamber can provide an indication where an ionizing particle has traversed the ionization chamber. Accordingly, two such modules comprising two ionization chambers only are sufficient to determine a trajectory of the ionizing particle. In contrast, the state-of-the-art, four ionization chambers are required to determine a trajectory of an ionizing particle. The ionizing particle detection module defined hereinbefore thus allows radiographic imaging systems that are more compact, lighter in weight and lower in cost.

The ionizing particle detection module as defined hereinbefore may comprise relatively few detection channels compared with a total number of possible traversing points that can be detected. That is, satisfactory spatial resolution may be achieved with relatively few detection channels. Given that a detection channel generally has a relatively high power consumption and is relatively costly, this translates into achieving satisfactory resolution within a power consumption budget and a cost budget that are relatively low.

The ionizing particle detection module as defined hereinbefore may be an attractive alternative for a detector that is based on scintillator bars. Radiographic imaging systems, in particular in muographs, that need to be portable may comprise detectors based on scintillator bars because these are relatively compact, relatively light in weight and consume relatively little power. However, these detectors have a relatively low spatial resolution. The ionizing particle detection module as defined hereinbefore may provide significantly better spatial resolution, while being compact, relatively light in weight and consuming relatively little power.

The ionizing particle detection module as defined hereinbefore may thus be used to advantage in applications where at least one of the following criteria is of importance: compactness, lightweight, ease of use, spatial resolution, low cost, and low power consumption. For example, the ionizing particle detection module may be used in a radiographic imaging system that is operated in a relatively small space, such as, for example, a cavity underground. Such an operation may be required in, for example, mining exploration or in archaeology. Another use example concerns inspection of objects, containers, such as, for example, nuclear waste casks. Instead of using a fixed scanning portal, such casks may be inspected by a portable radiographic imaging system, which may be battery-operated thanks to low power consumption. Moreover, compactness may make that the ionizing particle detection modules may be placed in a relatively narrow space between these casks, which may be densely packed.

Another advantage of the invention concerns reliability of detection. Noise, interference and other parasitic effects may make cause false detection of an ionizing particle, in particular when a multiplexing scheme is applied. In case detection involves two array of grids, an X grid and a Y grid, there are two possibilities of false localization in a two-dimensional plane. False detection may occur on the X grid or false detection may occur on the Y grid, or both. In contrast, in accordance with the invention, detection of an ionizing particle involves a matrix of detection pads, which constitutes the sole possibility of false localization in a two-dimensional plane. The likelihood of false localization is lower. What is more, the matrix of detection pads allows determining a shape of a cluster, which may assist in reliably deciding whether the cluster is most likely due to an ionizing particle or most likely caused by parasitic effects.

Yet another advantage of the invention concerns overall detection efficiency. A detector, which detects an ionizing particle traversing a plane, does so with a certain efficiency. Out of 100 ionizing particles traversing the plane, only a certain number, less than 100, will be detected, which may be expressed as a % of efficiency. The state-of-the-art method of detecting a trajectory of an ionizing particle requires at least 4 planes of detection: an upper X plane, an upper Y plane, a lower X plane, and a lower Y plane. In contrast, the invention claimed allows detecting the trajectory with only 2 detection planes provided by two detection modules as defined hereinbefore. Assuming that each of the aforementioned detection planes has a given efficiency of, for example, 90%, the invention claimed allows a higher detection efficiency, namely 81%, compared with the state-of-the art method, which has a detection efficiency of somewhat less than 66%.

For the purpose of illustration, some embodiments of the invention are described in detail with reference to accompanying drawings. In this description, additional features will be presented, some of which are defined in the dependent claims, and advantages will be apparent.

DESCRIPTION OF EMBODIMENT(S) OF THE INVENTION

Figure 1:
FIG. 1 is a block diagram of an ionizing particle detection module.
Figure 1:
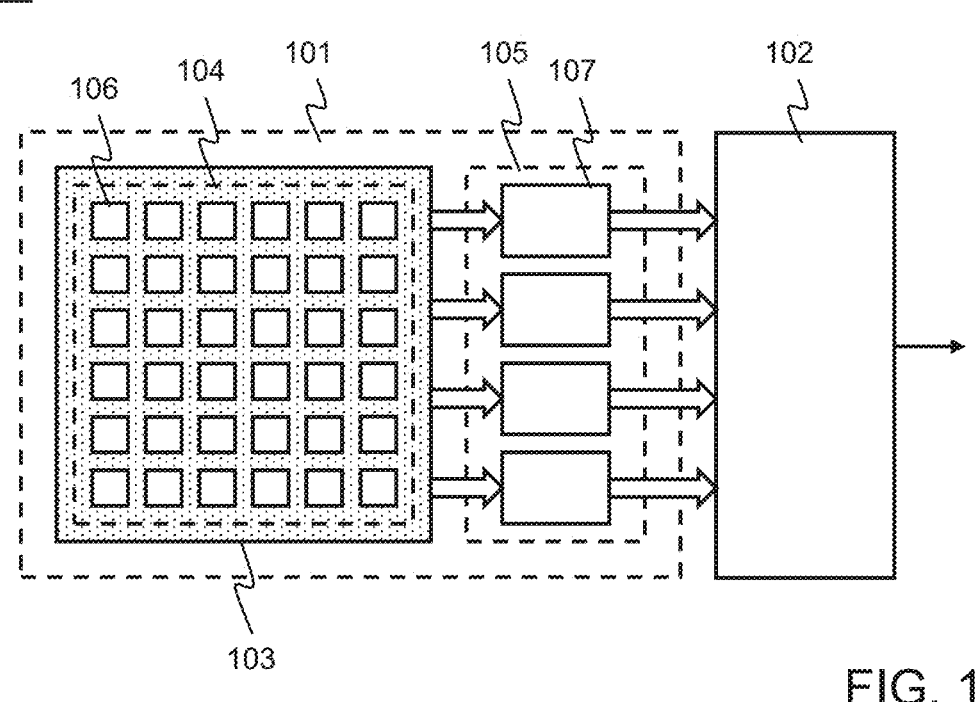

FIG. 1 schematically illustrates an ionizing particle detection module 100. FIG. 1 provides a very schematic block diagram of the ionizing particle detection module 100. The ionizing particle detection module 100 may be used, for example, in a so-called muograph, A muograph is a radiographic imaging system that images an object by detecting muons that have traversed the object to be imaged.

The ionizing particle detection module 100 comprises an ionizing particle detector 101 and a traversing point locator 102. The ionizing particle detector 101 comprises an ionization chamber 103, a matrix of detection pads 104 facing the ionization chamber 103, and a plurality of detection channels 105. A detection channel comprises a group of detection pads that may be electrically interconnected with each other. With respect to this, certain rules apply that will be described hereinafter. In FIG. 1, only one detection pad is denoted by a reference sign 106 and only one detection channel is denoted by a reference sign 107 for the sake of simplicity and clarity.

As mentioned hereinbefore, FIG. 1 is very schematic. The matrix of detection pads 104 may comprise any number of detection pads. FIG. 1 illustrates 6×6 detection pads merely for the sake of convenience. Likewise. FIG. 1 illustrates 4 detection channels merely for the sake of convenience. The number of detection channels will generally correspond with the number of detection pads divided by a multiplexing factor. This will be described in greater detail hereinafter.

The traversing point locator 102 may be implemented by means of a processor, or a set of processors, that is suitably programmed. The traversing point locator 102 carries out various operations that will be described hereinafter. A software program may define these operations.

Figure 2:
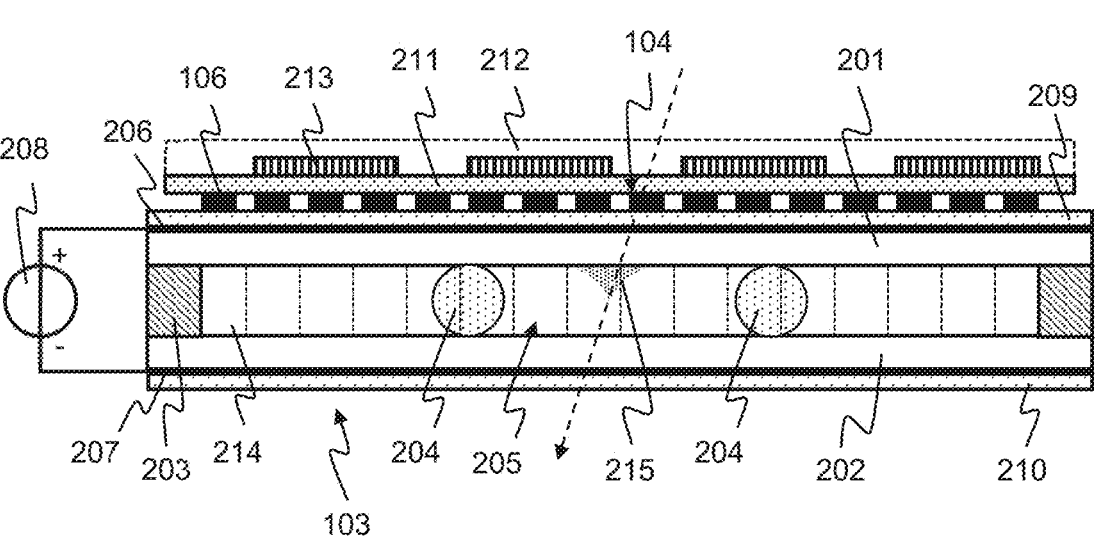
FIG. 2 is a schematic cross-sectional view of an ionizing particle detector in the ionizing particle detection module.

FIG. 2 schematically illustrates an embodiment of the ionizing particle detector 101, which forms part of the ionizing particle detection module 100 illustrated in FIG. 1. FIG. 2 provides a schematic cross-sectional view of this embodiment, which will also be referred to hereinafter as the ionizing particle detector 101 for the sake of convenience. The ionizing particle detector 101 may be housed in a casing, which is not represented in FIG. 2 for the sake of simplicity. The casing may comprise, for example, aluminum, carbon fiber material, or plastic material. The casing should preferably be outgas free.

In this embodiment, the ionization chamber 103 comprises a pair of parallel glass plates 201, 202. One of these glass plates 201 of which will be referred to hereinafter as upper glass plate 201, whereas the other glass plate 202 will be referred to as lower glass plate 202 for the sake of convenience. The upper glass plate 201 may have a surface area in the order of hundreds of square centimeters and a thickness between, for example, 0.5 mm and 3 mm. The lower glass plate 202 may have a similar surface area and a similar thickness. A gap between the pair of parallel glass plates 201, 202 may be between, for example, 1 mm and 3 mm.

The pair of parallel glass plates 201, 202 may be fixed to a frame 203. The frame 203 may be, for example, of fiber material. The ionization chamber 103 may further comprise spacers 204 between the pair of parallel glass plates 201, 202 as illustrated in FIG. 2. These spacers 204 may be ball shaped and made of, for example, ceramic material or polyether ether ketone, commonly denoted by the acronym PEEK. The spacers 204 contribute to uniformity of the gap between the pair of parallel glass plates 201, 202.

The gap between the pair of parallel glass plates 201, 202 is filled with an ionizable medium 205, which may be a gas. The ionizable medium 205 will be referred to hereinafter as ionizable gas 205 by way of illustration. The ionizable gas 205 may be, for example, a mixture of freon, isobutane, and sulfur hexafluoride (SF6), or any other suitable mixture. As an example, freon may be present in a proportion comprised between 95% and 99%, isobutane in a proportion between 1% and 5% and sulfur hexafluoride in a proportion between 0.1% and 2%. A mixture of 95.2% freon, 4.5% isobutane and 0.3% sulfur hexafluoride provided satisfactory results. The ionizable gas 205 preferably has a low degree of flamma-bility and a low degree of toxicity. It is further desirable that the ionizable gas 205 has a relatively low global warming potential.

The ionizable gas 205 may have a slight overpressure. That is, the ionizable gas 205 within the ionization chamber 103 may have a pressure that is slightly higher than the atmospheric pressure. Any leakage of the ionizable gas 205 then goes from the interior to the exterior, rather than in the opposite direction. This avoids contamination of the ioniz-able gas 205 within the ionization chamber 103.

The ionization chamber 103 is constructed so that it has a relatively high degree of gas tightness. The ionization chamber 103 may be constructed so that any leakage of the ionizable gas 205 occurs at a relatively low rate, which may be less than, for example, $10^{-9}$ mbar liter/second. This contributes to environmental safety. What is more, such a high degree of gas tightness may obviate a need for one or more gas bottles to compensate for leakage of the ionizable gas 205. In turn, this contributes to the portability of the ionizing particle detector 101.

A relatively high degree of gas tightness can be achieved in the following manner. A vacuum is created in the ioniza-tion chamber 103, in the gap between the pair of parallel glass plates 201, 202, before filling the ionization chamber 103 with the ionizable gas 205. Subsequently, points where leakage occurs may be identified using helium, or another suitable gas. These identified points are then treated to prevent leakage from occurring there. This process may be repeated once or several times.

The upper glass plate 201 has an outer side that is provided with a semi-conductive coating 206. Similarly, the lower glass plate 202 has an outer side that is provided with a coating 207, which may be semi-conductive too. The semi-conductive coating 206 on the upper glass plate 201 may comprise, for example, graphite, or antimony doped tin oxide. The semi-conductive coating 206 may have a thick-ness between, for example, 10 and 50 micrometers. The semi-conductive coating 206 may have a surface resistivity comprised between, for example, 0.5 MΩ/square and 10 MΩ/square. The semi-conductive coating 206 may be deposited on the upper glass plate 201 through, for example, painting or serigraphy. The aforementioned may also apply to the coating 207 on the lower glass plate 202.

A high-voltage source 208 applies a relatively high bias-ing voltage between the semi-conductive coating 206 on the upper glass plate 201 and the coating 207 on the lower glass plate 202. This biasing voltage may be, for example, between 5 and 15 kilovolt (kV). This generates a relatively strong electrical field in the ionization chamber 103, in the gap between the pair of parallel glass plates 201, 202 that is filled with the ionizable gas 205.

An electrically insulating layer 209 is present between the matrix of detection pads 104 and the semi-conductive coat-ing 206 on the upper glass plate 201. The electrically insulating layer 209 may be in the form of, for example, a mylar sheet. The electrically insulating layer 209 may have a thickness between, for example, 20 and 100 micrometer. An electrically insulating layer 210 may also cover the coating 207 on the lower glass plate 202. This electrically insulating layer 210 may be similar to that covering the semi-conductive coating 206 on the upper glass plate 201.

The matrix of detection pads 104, which faces the ion-ization chamber 103, is provided on a support structure 211.

The detection pads may be in the form of, for example, rectangular planar elements of conductive material, unlike strips used in conventional ionizing particle detectors. The support structure 211 may be in the form of, for example, a double-sided printed circuit board or a planar assembly of such boards with interconnections between these. The sup-port structure 211 will be referred to hereinafter as printed circuit board 211 by way of illustration. The matrix of detection pads 104 may thus be formed by appropriately etching a raw printed circuit board. A protective cover 212 may be applied to the printed circuit board 211 as illustrated in FIG. 2. The protective cover 212 may comprise, for example, polycarbonate.

The matrix of detection pads 104 is present on a side of a printed circuit board 211, which will be referred to hereinafter as lower side for the sake of convenience. Another side of the printed circuit board 211, which will be referred to as upper side, comprises electrical circuits 213. These electrical circuits 213 may be part of the plurality of detection channels 105 mentioned hereinbefore with refer-ence to FIG. 1. An electrical circuit of a detection channel may comprise, for example, a charge-sensitive amplifier, a discriminator circuit, a monostable circuit, and a driver circuit. The electrical circuits 213 may be in the form of application specific integrated circuits, commonly denoted by the acronym "ASIC".

The matrix of detection pads 104 may cover an area that is in the order of hundreds of square centimeters. For example, the area that is covered may be 16 cm×16 cm. The matrix of detection pads 104 may have a pitch comprised between, for example, 0.1 mm and 10 mm. FIG. 2 illustrates that respective detection pads cover respective zones in the ionization chamber 103. In FIG. 2, only one such zone is denoted by a reference sign 214. This zone 214 is covered by detection pad 106. The respective zones covered by the respective detection pads thus jointly constitute a matrix of relatively small blocks within the ionization chamber 103.

The ionization particle detector basically operates as follows. Let it be assumed that an ionizing particle, such as, for example, a muon traverses the ionization chamber 103. FIG. 2 illustrates such an event by means of an arrow in broken lines. The ionizing particle produces a local ioniza-tion 215 in the ionizable gas 205. In more detail, the ionizing particle generates initial free charge carriers. These trigger an avalanche of free charge carriers as a result of the relatively strong electrical field in the ionization chamber 103. The avalanche may extend over several respective neighboring zones in the ionization chamber 103 covered by respective neighboring detection pads as schematically illus-trated in FIG. 2. These neighboring detection pads covering the local ionization 215 form a cluster. The cluster will typically be two-dimensional due to the fact that the matrix of detection pads 104 is a two-dimensional array. The detection pads are comprised in a plane and arranged in rows and columns. Thus, in a cluster, a detection pads may have neighboring detection pads in row direction and in column direction.

A cluster of detection pads covering a local ionization has a typical size that depends on various factors. One of these factors concerns the pitch of the detection pads and their size. The smaller the pitch is, the more detection pads the cluster will typically comprise. Another factor concerns the gap between the pair of parallel glass plates 201, 202, its size. Yet another factor, concerns the biasing voltage applied between the pair of parallel glass plates 201, 202. Yet another factor concerns the ionizable gas 205, its composi-tion. All these factors may thus be used to tune, as it were, the typical size of a cluster of detection pads covering a location ionization produced by an ionizing particle traversing the ionization chamber 103.

For example, the ionizable gas 205 may comprise so-called quenchers that absorb electrons and photons. The quenchers have a widening effect on the avalanche. The widening effect may depend on proportions in which quenchers are present in the ionizable gas 205, as well as the type of quenchers used. In the mixture mentioned hereinbefore, isobutane and sulfur hexafluoride are quenchers.

A local ionization induces a pulse-like signal in a detection pad covering a zone where the local ionization occurs. This pulse-like signal is typically relatively weak and relatively short in duration. For example, the pulse-like signal may have a leading edge in the order of tenths of nanoseconds, a trailing edge in the order of nanoseconds and a total duration in the order of nanoseconds too. For example, the leading edge may be about 0.2 ns, the trailing edge may be about 2 ns, and the total duration may be about 3 to 4 ns.

The semi-conductive coating 206 on the upper glass plate 201 plays a role with regard to pulse-like signals that are induced in a cluster of detection pads covering a local ionization. First of all, the semi-conductive nature of this coating 206 allows that pulse-like signals are induced or, more precisely, that these signals are induced such that these can be sufficiently reliably detected. The pulse-like signals may be sufficiently reliably detected if the semi-conductive coating 206 has a surface resistivity comprised between, for example, 0.5 MΩ/square and 10 MΩ/square, about 2 MΩ/square has been found to be a suitable resistivity. Finding a suitable resistivity may involve a compromise. On the one hand, the lower the resistivity is, the higher the rate at which ionizing particles may follow each other and be reliably detected. On the other hand, the higher the resistivity is, the less crosstalk there will be between respective pulse-like signals induced in respective neighboring detection pads.

A detection channel of which a detection pad produces a pulse-like signal processes this signal so as to provide an indication of local ionization as an output. This processing may involve relatively sensitive and fast electronics given that the pulse-like signal is typically relatively weak and relatively short in duration, as discussed hereinbefore. For example, an input amplifier may need to have a charge sensitivity in the order of a few mV/fC and be capable of handling transients in the order of a few hundreds of picoseconds. In general, the relatively sensitive and fast electronics in a detection channel is relatively costly and has a relatively high power consumption. Accordingly, it is desirable that the ionizing particle detection module 100 comprises relatively few detection channels while providing sufficiently high resolution. These objectives may be achieved with the ionizing particle detection module 100 described herein, as will be apparent from what follows.

As mentioned hereinbefore, a detection channel comprises a group of detection pads that may be electrically interconnected with each other. Accordingly, in case the detection channel provides an indication of local ionization, the local ionization may have occurred in any one of the respective zones in the ionization chamber 103 covered by the respective detection pads in the group that belongs to the detection channel. That is, it is not possible to determine the zone in the ionization chamber 103 where local ionization has occurred on the sole basis of the indication provided by the detection channel.

As explained hereinbefore, a local ionization induces pulse-like signals in a cluster of detection pads. These pulse-like signals are induced almost simultaneously. Consequently, in case a local ionization occurs, several detection channels will almost simultaneously receive and process these pulse-like signals. A detection channel that is the first to receive one of the pulse-like signals may cause a time window to be opened. This pulse-like signal and subsequent pulse-like signals within this time window, which are received and processed by other detection channels, may then be considered as induced in a cluster of detection pads. The time window may be, for example, in the order of a few tens of nanoseconds, such as, for example, 80 ns. Thus, a local ionization produced by an ionizing particle traversing the ionization chamber 103 will typically cause several detection channels to simultaneously provide, or almost simultaneously provide, indications of local ionization.

Given the foregoing, a reliable indication of where a local ionization has occurred in the ionization chamber 103 may be provided on the basis of the following two data. First, respective zones in the ionization chamber 103 where the local ionization may have potentially occurred have been identified. Namely, these respective zones are those that are covered by the respective detection pads belonging to the several detection channels that have provided the indications of local ionization. Secondly, it is known that a cluster of detection pads covers the local ionization and, moreover, the size that this cluster typically has is also known. Accordingly, it may then be determined if there are detection pads forming a cluster among the respective detection pads belonging to the several detection channels that have provided the indications of local ionization. It may then be determined if such a cluster has a size that corresponds with the size that is typical for local ionization, or at least that the size of the cluster is sufficiently close to the typical size.

Figure 3:
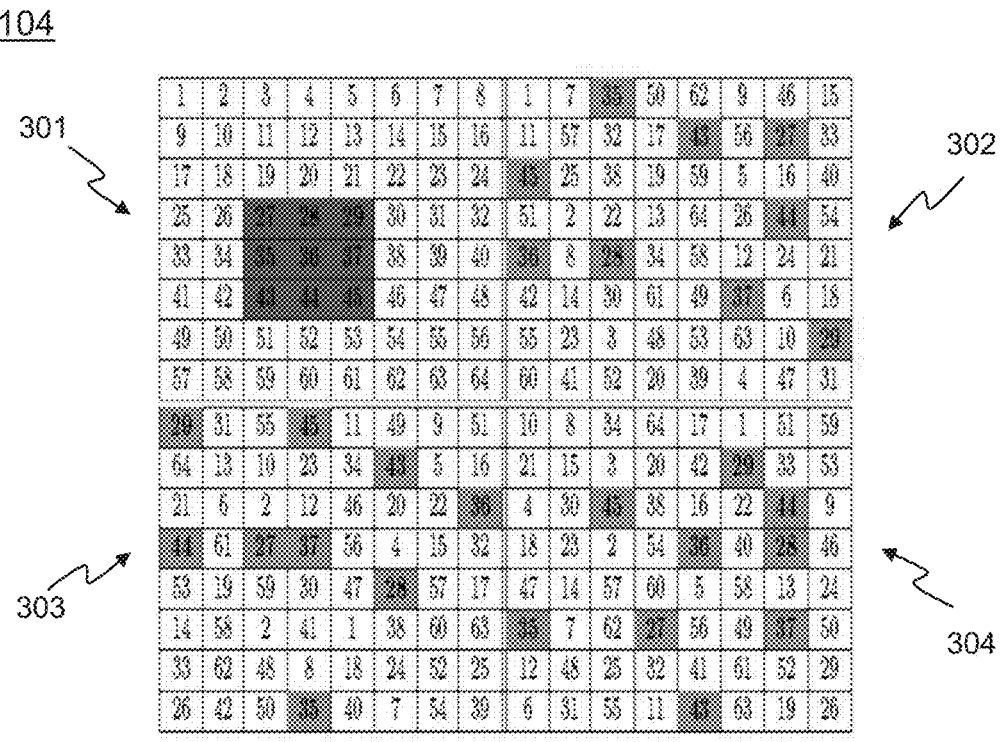
FIG. 3 is a schematic top view of a matrix of detection pads in the ionizing particle detector with numeral references indicating detection channels to which the detection pads belong.

FIG. 3 very schematically illustrates an embodiment of the matrix of detection pads 104 with reference numerals indicating detection channels. FIG. 3 provides a schematic top view of this embodiment, which will also be referred to hereinafter as the matrix of detection pads 104 for the sake of convenience. The detection pads are represented as relatively small rectangles, whereby a single rectangle represents a single detection pad. In this embodiment, the matrix 104 comprises 16×16 detection pads making a total of 256 detection pads. There are 64 detection channels, four times less than the total of detection pads. The detection channels are represented as reference numerals in the rectangles representing the detection pads. A reference numeral in a rectangle representing a detection pad indicates the detection channel to which the detection pad belongs.

Thus, for example, an upper left rectangle in FIG. 3 represents an upper left detection pad in the matrix 104. The upper left rectangle comprises reference numeral 1, which indicates that the upper left detection pad belongs to detection channel 1. An upper right rectangle in FIG. 3 represents an upper right detection pad in the matrix 104. The upper right rectangle comprises reference numeral 15, which indicates that the upper right detection pad belongs to detection channel 15. A lower left rectangle in FIG. 3 represents a lower left detection pad in the matrix 104. The lower left rectangle comprises reference numeral 26, which indicates that the lower left detection pad belongs to detection channel 26. A lower right rectangle in FIG. 3 represents a lower right detection pad in the matrix 104. The lower right rectangle comprises reference numeral 26, which indicates that the lower right detection pad also belongs to detection channel 26. The last two mentioned detection pads thus belong to the same detection channel.

The detection pads in the matrix 104 are organized in mutually exclusive groups of four detection pads that belong to a same detection channel. Thus, detection channel 1 comprises four detection pads, namely the four detection pads represented as rectangles having the reference 1. Likewise, detection channel 2 comprises four detection pads, namely the four detection pads represented as rectangles having reference 2, and so on. This organization provides a multiplexing factor of four: the 256 detection pads are assigned to the 64 detection channels. Each detection channel comprises a group of four detection pads, whereby these groups are mutually exclusive. The four detection pads that belong to a same detection channel may be electrically interconnected with each other on the printed circuit board 211 illustrated in FIG. 2.

The following rules apply with regard to the manner in which the detection pads and the detection channels are organized. Firstly, the detection pads of a detection channel are nonadjacent and dispersed throughout the matrix 104. Secondly, two detection channels have a maximum of two detection pads next to each other in the matrix 104. One of the two detection pads belongs to one of the two detection channels, the other of the two detection pads belonging to the other of the two detection channels. It should be noted that FIG. 3 illustrates one possible scheme of organizing the detection pads and the detection channels according to these rules. Many other schemes that satisfy these rules may be devised.

In the scheme illustrated in FIG. 3, the matrix of detection pads 104 may be regarded as being divided into four submatrices: an upper left submatrix 301, an upper right submatrix 302, a lower left submatrix 303, and a lower right submatrix 304. These four submatrices are equal in size, each comprising 8×8 detection pads. The number of submatrices corresponds with the aforementioned multiplexing factor, which is four. The scheme illustrated in FIG. 3 provides that a detection pad of a detection channel uniquely belongs to one among the four submatrices. Accordingly, in each of the four submatrices, a reference numeral indicating a detection channel only occurs once. This technique of organizing the detection pads and the detection channels through a division of the matrix 104 contributes to achieving a scheme that allows reliable detection.

The size and the pitch of the detection pads in the matrix 104 are such that a local ionization produced by an ionizing particle traversing the ionization chamber 103 typically induces pulse-like signals in a cluster of 3×3 detection pads. That is, a typical cluster size for a local ionization is 3×3. As explained hereinbefore, the typical cluster size depends on other factors, which, referring to FIG. 2, include the gap between the pair of parallel glass plates 201, 202, its size, the biasing voltage applied between the pair of parallel glass plates 201, 202, and the ionizable gas 205, its composition. All these factors, together with the size and the pitch of the detection pads, have thus been set to make that the typical cluster size for a local ionization is 3×3 in this embodiment.

In FIG. 3, a 3×3 cluster of detection pads is indicated by means of a dark gray shading. This 3×3 cluster is present in the upper left submatrix 301. The 3×3 cluster is centered on a detection pad in this submatrix that belongs to detection channel 36. The 3×3 cluster comprises 8 other detection pads that surround this center detection pad. These 8 other detection pads of the 3×3 cluster belong to detection channels 27, 28, 29, 35, 37, 43, 44, and 45, respectively. The detection pads of this 3×3 cluster cover a local ionization produced by an ionizing particle traversing the ionization chamber 103 at a location proximate to a zone covered by the center detection pad of the 3×3 cluster. Thus, in this example, the typical size of a cluster of detection pads covering a local ionization is nine. A local ionization typically induces pulse-like signals in nine mutually neighboring detection pads, which form a cluster.

FIG. 3 indicates, by means of a light gray shading, further detection pads that belong to the aforementioned detection channels 27, 28, 29, 35, 37, 43, 44, and 45, but that are not part of the aforementioned 3×3 cluster. These further detection pads are located in the other submatrices, namely the upper right submatrix 302, the lower left submatrix 303, and the lower right submatrix 304. The further detection pads may form accidental clusters. For example, the lower left submatrix 303 comprises an accidental cluster of two further detection pads that belong to the detection channels 27 and 37. This accidental cluster thus has a size of two. The lower right submatrix 304 comprises an accidental cluster of three further detection pads that belong to the detection channels 28, 29, and 44. This accidental cluster thus has a size of three. For the rest, there are relatively many isolated further detection pads, which may be considered as accidental clusters having the size of one.

Figure 4:
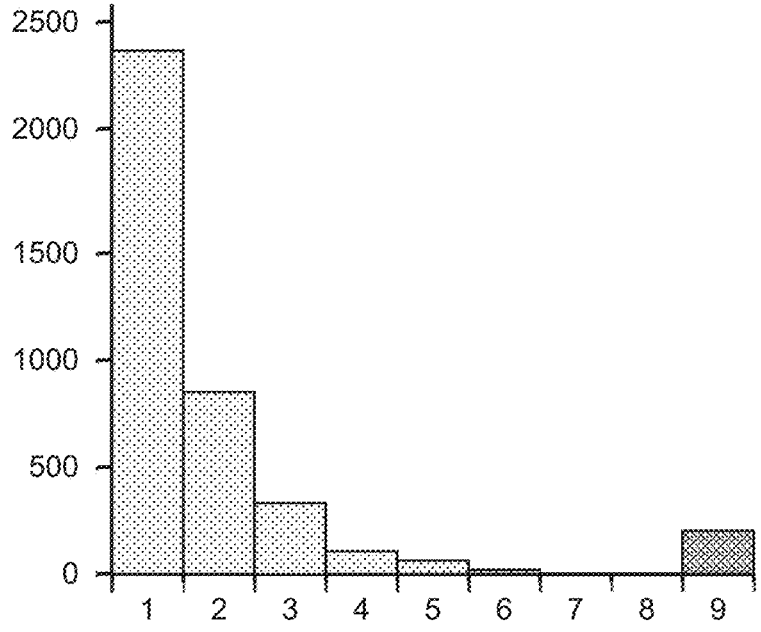
FIG. 4 is a histogram cluster sizes, which relates to the matrix of detection pads and the detection channels to which these belong as represented in FIG. 3.

FIG. 4 is a histogram of cluster sizes, which relates to the matrix of detection pads 104 and the detection channels to which these belong as represented in FIG. 3. The histogram has been obtained in the following manner. A series of 196 ionizing particles is assumed to consecutively traverse the ionization chamber 103. Each ionizing particle traverses the ionization chamber 103 in a different zone among 196 respective zones covered by 196 respective detection pads that are not at the boundary of the matrix 104 illustrated in FIG. 3. The number of 196 is related to the matrix 104 comprising 16×16 detection pads and the typical cluster size for a local ionization being 3×3 as mentioned hereinbefore. This makes that there are 196 detection pads in the matrix 104 that may form a center detection pad of a 3×3 cluster of detection pads.

Thus, referring to FIG. 3, a first ionizing particle may traverse the ionization chamber 103 in a zone covered by the detection pad in the upper left submatrix 301 and belonging to detection channel 10. A second ionizing particle may traverse the ionization chamber 103 in the zone covered by the detection pad in the upper left submatrix 301 and belonging to detection channel 11. Continuing this scheme, the final, $196^{th}$ ionizing particle traverses the detection pad in the lower right submatrix 304 and belonging to detection channel 52.

Each of the 196 ionizing particles traversing the ionization chamber 103 is assumed to produce a local ionization that is covered by a 3×3 cluster of detection pads, that is, a cluster of size 9. Consequently, for each traversing ionizing particle, there are nine detection channels that provide a local ionization indication. As mentioned hereinbefore, each detection channel comprises a group of four detection pads, whereby respective groups of detection pads belonging to respective detection channels are mutually exclusive. Consequently, for each ionizing particle traversing the ionization chamber 103 there are 36 detection pads among which clusters are present as described hereinbefore with reference to FIG. 3. The clusters are identified and a count is made for each cluster size ranging from 1 to 9. The histogram illustrated in FIG. 4 is obtained by making this count for each of the 196 ionizing particles that consecutively traverse the ionization chamber 103, as assumed.

In the histogram illustrated in FIG. 4, the clusters counted for the sizes 1 to 8 may be regarded as accidental clusters. This is because the histogram has been obtained on the basis of a postulate that each particle traversing the ionization chamber 103 produces a local ionization that is covered by a cluster of the detection pads having a size of nine. Consequently, any cluster that has a different size does not cover the local ionization and may therefore be regarded as accidental. Conversely, the clusters counted for the size 9 may be regarded as genuine clusters in the sense that these clusters indicate where the local ionization occurs in the ionization chamber 103.

The histogram illustrated in FIG. 4 illustrates that the genuine clusters and the accidental clusters are clearly distinguishable. There are relatively few clusters, or even no clusters at all, that have the size 7 or 8, relatively close to the size 9 of the genuine clusters. The histogram thus shows that is possible to identify a location where an ionizing particle traverses the ionization chamber 103 in a reliable and precise manner despite use of a multiplexing scheme. The multiplexing scheme consists in assigning a group of detection pads to a same detection channel as described hereinbefore. Thus, there are significantly fewer detection channels than if the multiplexing scheme were not used. Use of fewer detection channels translates into lower cost and less power consumption.

The traversing point locator 102 illustrated in FIG. 1 carries out the following operations. The traversing point locator 102 identifies clusters among detection pads belonging to detection channels simultaneously providing indications of local ionization. For example, the traversing point locator 102 may identify the clusters mentioned hereinbefore that are illustrated in FIG. 3. These clusters comprise a cluster of size 9, a cluster of size 3, a cluster of size 2 and 22 clusters of size 1.

The traversing point locator 102 provides a traversing point indication on the basis of a cluster that has been identified if the cluster satisfies at least the following size criterion: the cluster comprises a predefined minimum number of detection pads. Referring again to FIG. 3 by way of illustration, the predefined minimum number may be 8 or 9. Thus, the traversing point locator 102 may thus provide a traversing point indication on the basis of the 3×3 cluster that is indicated by the dark gray shading in this figure. The traversing point indication may correspond with a center position in this cluster. In case respective weighing factors are provided for respective indications of local ionization, the traversing point locator 102 may use these weighing factors in providing the traversing point indication. The respective weighing factor may be based on, for example, respective amplitudes on pulse-like signals that are induced in respective detections pads of the cluster.

The traversing point locator 102 may apply a shape criterion in addition to the size criterion in providing a traversing point indication, A cluster due to an ionizing particle will generally have a typical cluster shape. In this example, the typical cluster shape may be defined as having a similar size in row direction and in column direction. The typical cluster shape may further be defined as being rather symmetrical with respect to a traversing line in row direction and a traversing line in column direction. In case a cluster has a shape that is sufficiently similar to the typical cluster, the traversing point indication is validated and thus provided. Conversely, in case a cluster has a shape that differs too much from the typical cluster shape, the traversing point indication may be invalidated and thus not provided, even if the cluster respects the size criterion.

The ionizing particle detection module 100 described hereinbefore with reference to FIG. 1-4 may be used in a radiographic imaging system, such as, for example a muograph based on detection and localization of muons. Basically, the radiographic imaging system collects respective traversing point indications that the ionizing particle detection module 100 provides over time, during a period that will be referred to as imaging period. The radiographic imaging system may then form an image on the basis of these collected traversing point indications.

Figure 5:
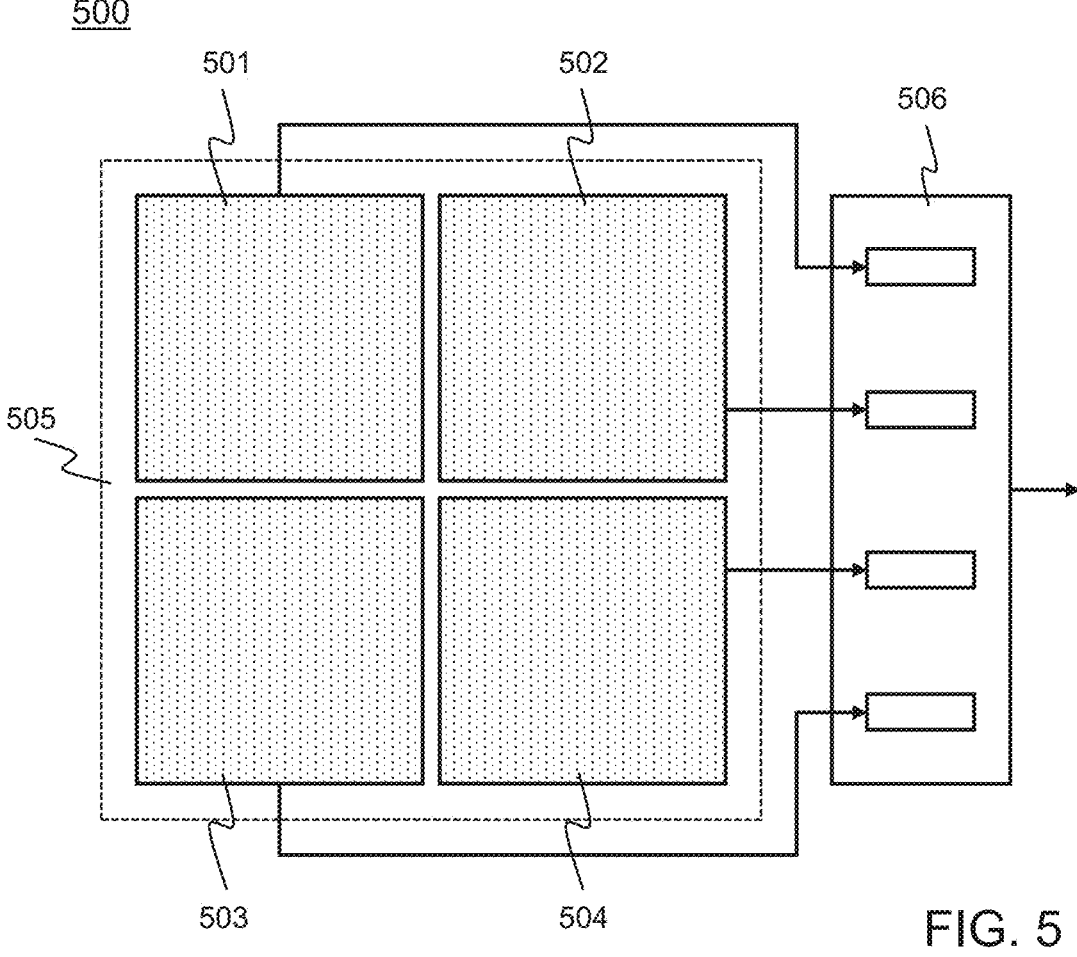
FIG. 5 is a schematic block diagram of an assembly of ionizing particle detection modules arranged in a same plane.

FIG. 5 schematically illustrates an assembly 500 of ionizing particle detection modules 501, 502, 503, 504 arranged in a same plane 505. FIG. 5 provides a schematic block diagram of this assembly. The ionizing particle detection modules 501, 502, 503, 504 may each correspond with the ionizing particle detection module 100 described hereinbefore with reference to FIGS. 1 to 4. The ionizing particle detector 101 thereof may be configured as a basic building block so that it can be coupled to one or more other ionizing particle detectors. Accordingly, a larger detection surface may be obtained that comprises a larger number of detection pads, which may offer higher resolution. Thus, a plurality of ionizing particle detection modules may form a modular system. The assembly 500 illustrated in FIG. 5 comprises four ionizing particle detection modules 501, 502, 503, 504 by way of illustration. Such an assembly may comprise more or fewer ionizing particle detection modules than four.

FIG. 5 schematically illustrates that the assembly 500 of ionizing particle detection modules 501, 502, 503, 504 may comprise a general traversing point locator 506. The general traversing point locator 506 may functionally provide the traversing point locator for each ionizing particle detection module 501, 502, 503, 504. For example, the general traversing point locator 506 may be a single processor that executes a software program causing this processor to carry out the operations described hereinbefore for identifying where an ionizing particle has traversed the ionization chamber of an ionizing particle detector. In addition, the general traversing point locator 506 identifies the ionizing particle detector whose ionization chamber has been traversed. This identification may consist in detecting the ionizing particle detector of which the detection channels produce indications of local ionization. The assembly of ionizing particle detection modules 501, 502, 503, 504 illustrated in FIG. 5 may thus be functionally equivalent to a relatively large ionizing particle detection module that has four times more detection pads than a single one of the particle detection modules 501, 502, 503, 504 in the assembly illustrated in FIG. 5.

Figure 6:
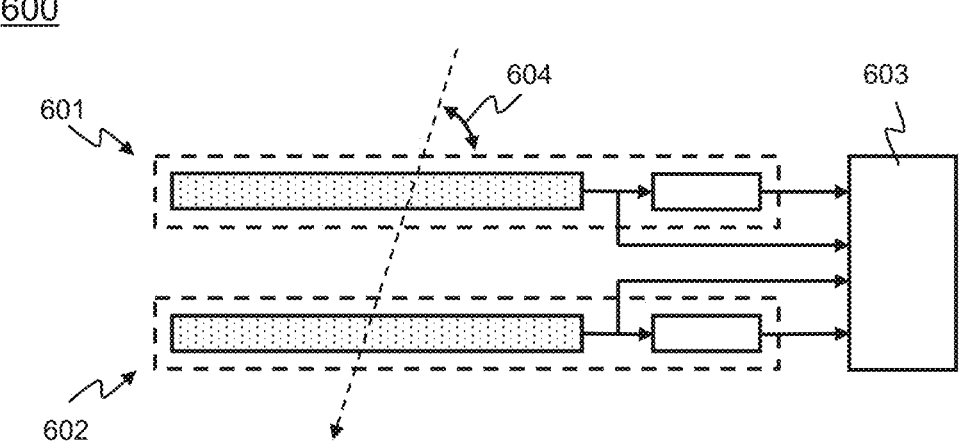
FIG. 6 is a schematic block diagram of a radiographic imaging system comprising two ionizing particle detection modules that are juxtaposed.

FIG. 6 illustrates a radiographic imaging system 600 comprising two ionizing particle detection modules 601, 602 that are juxtaposed. FIG. 6 provides a schematic block diagram of this radiographic imaging system 600. The two ionizing particle detection modules 601, 602 may each correspond with the ionizing particle detection module 100 described hereinbefore with reference to FIGS. 1 to 4. One of the two ionizing particle detection modules 601, 602 will be referred to hereinafter as upper ionizing particle detection module 601 for the sake of convenience. The other one will be referred to as lower ionizing particle detection module 602.

The radiographic imaging system 600 further comprises an imaging module 603. The imaging module 603 is coupled to receive traversing point indications from the upper ionizing particle detection module 601 and traversing point indications from the lower ionizing particle detection module 602. The imaging module 603 is further coupled to receive indications of local ionization from the detection channels in the upper ionizing particle detection module 601 and from the detection channels in the lower ionizing particle detection module 602. The imaging module 603 may comprise a processor into which a software program has been loaded defining operations that the processor may carry out. This processor may be the same as the ones mentioned hereinbefore, which implement the operations for identifying where an ionizing particle has traversed an ionization chamber 103.

The radiographic imaging system 600 basically operates as follows. Let it be assumed that an ionizing particle first traverses the upper ionizing particle detection module 601 and then the lower ionizing particle detection module 602. FIG. 6 illustrates such an event by means of an arrow in broken lines. In this case, the imaging module 603 will first receive indications of local ionization from the detection channels in the upper ionizing particle detection module 601 After a relatively short delay, the imaging module 603 will receive indications of local ionization from the detection channels in the lower ionizing particle detection module 602. The aforementioned delay may be in the order of several hundreds of picoseconds. For example, a muon needs 3 ns to travel over 1 m. In case the two ionizing particle detection modules 601, 602 are separated by a distance of, for example, about 20 cm, the delay will be about 600 ps.

The imaging module 603 may obtain a direction indication for the ionizing particle by determining in which one of the two ionizing particle detection modules 601, 602, the detection channels were first to provide indications of local ionization. In the case presented in FIG. 6, the direction indication indicates that the ionizing particle has a downward oriented trajectory. The direction indication may be relevant to distinguish between ionizing particles, such as, for example, muons, coming from the atmosphere or from the Earth's surface.

The imaging module 603 may determine a trajectory 604 of the ionizing particle traversing the two particle detection modules as illustrated in FIG. 6 by means of the arrow in broken lines. The upper ionizing particle detection module 601 provides a traversing point indication indicating an upper traversing point, which is where the ionizing particle has traversed the ionization chamber of the aforementioned module 601. Almost simultaneously, given the aforementioned relatively short delay, the lower ionizing particle detection module 602 also provides a traversing point indication indicating a lower traversing point, which is where the ionizing particle has traversed the ionization chamber of the aforementioned module 602. The imaging module 603 may then calculate an angle of incidence in azimuth direction and an angle of incidence in elevation direction given the upper traversing point, the lower traversing point, and the distance that separates the two particle detection modules. These angles of incidence indicate the trajectory 604 of the ionizing particle.

The imaging module 603 may define a map in which respective positions represent respective trajectories that the imaging module 603 may potentially determine. This map may be blank at the start of an imaging period in the sense that each position has a zero count. The imaging module 603 may then make a count for each position in the map during the imaging period. The count for a position indicates a number of times that an ionizing particle has traversed the two ionizing particle detection modules 601, 602 with a trajectory represented by the position concerned in the map. At the end of the imaging period, the map is complete and constitutes a measurement map. This measurement map be compared with a reference map. The reference map may correspond with a map that is obtained in the absence of any object that ionizing particles reaching the two particle detection modules may have traversed. An image of an object may be obtained on the basis of this comparison of the measurement map with the reference map.

The radiographic imaging system 600 described hereinbefore with reference to FIG. 6 is configured for absorption-based muography. In absorption-based muography, muons are detected on one side with respect to an object to be imaged. Imaging is based on a probability for a muon to pass through the object. Absorption-based muography may be used, for example, for imaging an overburden from inside a tunnel. Absorption-based muography may also be used for imaging an object that is relatively distant and that may be relatively large. In such an application, precision in determining where a muon traverses a detector is an important performance factor.

The ionizing particle detection module 100 described hereinbefore may also be used in a radiographic imaging system 600 configured for scattering-based muography. In scattering-based muography, a trajectory of a muon is detected before and after passing an object to be imaged so as to measure a change of trajectory. Thus, a radiographic imaging system configured for scattering-based muography may comprise two ionizing particle detection modules as described hereinbefore that are placed at one side of an object to be imaged and two further ionizing particle detection modules placed at an opposite side of the object. The change in trajectory may be measured by comparing the trajectory of muon detected by the two ionizing particle detection modules at the one side of the object and the trajectory detected by the two further ionizing particle detection modules at the other side of the object. Such a radiographic imaging system may be used, for example, for imaging relatively small objects, which may comprise nuclear material.

The embodiments described hereinbefore with reference to the drawings are presented by way of illustration. The invention may be implemented in numerous different ways. In order to illustrate this, some alternatives are briefly indicated.

The invention may be applied in numerous types of products or methods related to radiographic imaging based on detection of ionizing particles.

There are numerous different ways of implementing an ionizing particle detection module in accordance with the invention. The embodiments presented hereinbefore comprise a matrix of 16×16 detection pads, which is subdivided into four submatrices for the purpose of assigning detection pads to detection channels. In other embodiments, a matrix may comprise more or fewer detection pads and the matrix may be divided into more or fewer submatrices.

The remarks made hereinbefore demonstrate that the embodiments described with reference to the drawings illustrate the invention, rather than limit the invention. The invention can be implemented in numerous alternative ways that are within the scope of the appended claims. All changes that come within the meaning and range of equivalency of the claims are to be embraced within their scope. Any reference sign in a claim should not be construed as limiting the claim. The verb "comprise" in a claim does not exclude the presence of other elements or other steps than those listed in the claim. The same applies to similar verbs such as "include" and "contain". The mention of an element in singular in a claim pertaining to a product, does not exclude that the product may comprise a plurality of such elements. Likewise, the mention of a step in singular in a claim pertaining to a method does not exclude that the method may comprise a plurality of such steps. The mere fact that respective dependent claims define respective additional features, does not exclude combinations of additional features other than those reflected in the claims.

The invention claimed is:

1. An ionizing particle detection module comprising:
an ionizing particle detector comprising:
an ionization chamber adapted to produce a local ionization in an ionizable medium within the ionization chamber in response to an ionizing particle traversing the ionization chamber;
a matrix of detection pads being a two-dimensional array in which the detection pads are comprised in a plane and arranged in rows and columns, the matrix of detection pads facing the ionization chamber so that respective detection pads cover respective zones in the ionization chamber;
a plurality of detection channels wherein respective detection channels comprise respective mutually exclusive groups of detection pads according to the following rules:
the detection pads of a detection channel are nonadjacent and dispersed throughout the matrix;
two detection channels have a maximum of two detection pads next to each other in the matrix, one of the two detection pads belonging to one of the two detection channels, the other of the two detection pads belonging to the other of the two detection channels,
a detection channel being adapted to provide an indication of a local ionization occurring somewhere within the respective zones in the ionization chamber covered by the respective detection pads of the detection channel;
a traversing point locator adapted to identify a cluster among the detection pads belonging to detection channels simultaneously providing indications of local ionization, and adapted to provide a traversing point indication on the basis of the cluster that has been identified if the cluster comprises a predefined minimum number of detection pads, the traversing point indication indicating where the ionizing particle has traversed the ionization chamber.

2. An ionizing particle detection module according to claim 1, wherein a detection channel comprises N detection pads, N being an integer number, a detection pad of the detection channel uniquely belonging to a submatrix among N submatrices into which the matrix of detection pads can be divided.

3. An ionizing particle detection module according to claim 1, wherein the matrix of detection pads cover an area that is in the order of hundreds of square centimeters.

4. An ionizing particle detection module according to claim 1, wherein the detection pads in the matrix of detection pads have a pitch comprised between 0.1 mm and 10 mm.

5. An ionizing particle detection module to claim 1, wherein the matrix of detections pads is present on one side of a support structure, another side of the support structure comprising electrical circuits of the detection channels.

6. An ionizing particle detection module according to claim 1, wherein the ionization chamber comprises a pair of parallel glass plates.

7. An ionizing particle detection module to claim 1, wherein at least one of the parallel glass plates comprises a semi-conductive coating.

8. An ionizing particle detection module according to claim 1, wherein the ionizable medium comprises quenchers that absorb electrons and photons.

9. A radiographic imaging system adapted to image an object based on detection of ionizing particles that have traversed the object, the radiographic imaging system comprising at least one ionizing particle detection module according to claim 1.

10. A radiographic imaging system according to claim 9, comprising two ionizing particle detection modules that are juxtaposed.

11. A radiographic imaging system according to claim 10, adapted to provide an angle of incidence indication for the detected ionizing particle on the basis of the traversing point indication provided by the traversing point locator in one of the two ionizing particle detection modules and the traversing point indication provided by the traversing point locator in the other of the two ionizing particle detection modules.

12. A radiographic imaging system according to claim 10, adapted to provide a direction indication for the detected ionizing particle by determining in which one of the two ionizing particle detection modules, the detection channels were first to provide indications of local ionization.

13. A radiographic imaging system according to claim 9, comprising a plurality of ionizing particle detectors adapted to be contiguously arranged in a same plane.

14. Use of a radiographic imaging system according to claim 9 for imaging an object, whereby muons constitute the ionizing particles that traverse the object and that are detected.

15. A method of radiographic imaging based on detection of ionizing particles that have traversed an object to be imaged, wherein use is made of:
an ionizing particle detector comprising:
an ionization chamber adapted to produce a local ionization in an ionizable medium within the ionization chamber in response to an ionizing particle traversing the ionization chamber;
a matrix of detection pads being a two-dimensional array in which the detection pads are comprised in a plane and arranged in rows and columns, the matrix of detection pads facing the ionization chamber so that respective detection pads cover respective zones in the ionization chamber;
a plurality of detection channels wherein respective detection channels comprise respective mutually exclusive groups of detection pads that are electrically interconnected with each other according to the following rules:
the detection pads of a detection channel are nonadjacent and dispersed throughout the matrix;
two detection channels have a maximum of two detection pads next to each other, one of the two detection pads belonging to one of the two detection channels, the other of the two detection pads belonging to the other of the two detection channels,
a detection channel being adapted to provide an indication of a local ionization occurring somewhere within the respective zones in the ionization chamber covered by the respective detection pads of the detection channel,
the method comprising:
identifying a cluster of detection pads among the detection pads belonging to detection channels simultaneously providing indications of local ionization; and
providing a traversing point indication on the basis of the cluster that has been identified if the cluster comprises a predefined minimum number of detection pads, the traversing point indication indicating where the ioniz-
ing particle has traversed the ionization chamber.

\* \* \* \* \*